United States Patent [19]

Fujita et al.

[11] Patent Number: 5,688,854

[45] Date of Patent: Nov. 18, 1997

[54] PRODUCTION OF METHYLAMINES

[75] Inventors: Takeyuki Fujita; Kiyonobu Niwa; Kazumoto Ogura; Michio Fukatsu, all of Tokyo-to, Japan

[73] Assignee: Nitto Kagaku Kogyo Kabushiki Kaisha, Tokyo, Japan

[21] Appl. No.: 712,886

[22] Filed: Sep. 12, 1996

[30] Foreign Application Priority Data

| Sep. 14, 1995 | [JP] | Japan | 7-260914 |
| Oct. 12, 1995 | [JP] | Japan | 7-289207 |
| Sep. 4, 1996 | [JP] | Japan | 8-252219 |
| Sep. 4, 1996 | [JP] | Japan | 8-252220 |

[51] Int. Cl.$^6$ .................................................. C07L 209/16
[52] U.S. Cl. .............................................................. 564/479
[58] Field of Search ....................................... 564/479, 478, 564/480

[56] References Cited

U.S. PATENT DOCUMENTS

| 4,398,041 | 8/1983 | Cochran et al. | 564/479 |
| 4,814,503 | 3/1989 | Abrams et al. | 564/474 |
| 5,382,696 | 1/1995 | Kiyoura et al. | 564/479 |
| 5,488,165 | 1/1996 | Hutchin et al. | 564/479 |
| 5,569,785 | 10/1996 | Kourtakis et al. | 564/474 |

*Primary Examiner*—Brian M. Burn
*Attorney, Agent, or Firm*—Wenderoth, Lind & Ponack

[57] ABSTRACT

Disclosed is an improvement in a process for catalytic production of methylamines from methanol and $NH_3$, or methanol, a mixture of methylamines and $NH_3$, or a mixture of methylamines and $NH_3$, in a gaseous phase, over a bed of a zeolite catalyst, where the improvement is that the catalyst bed is divided into two or more sub-beds, and the difference between the inlet and outlet temperatures of each catalyst sub-bed is kept in the range of approximately 5° C. to approximately 70° C. while the reaction is carried out.

13 Claims, 1 Drawing Sheet

PRODUCTION OF METHYLAMINES

BACKGROUND OF THE INVENTION

1. Field of the Invention

The present invention relates to a process for producing methylamines, utilizing the vapor phase catalytic reaction between methanol and ammonia. More particularly, the present invention relates to a process for producing methylamines using a zeolite as a catalyst, by which process it is made possible to more effectively utilize high dimethylamine selectivity characteristic of zeolite catalysts.

Dimethylamine is an important chemical intermediate useful as the starting material of various solvents, pharmaceuticals, rubber chemicals, surface active agents and the like.

2. Related Art

Typically, dimethylamine is produced by allowing methanol to react, in a gaseous phase, with ammonia at a high temperature (approximately 400° C.) in the presence of a solid acid catalyst, such as alumina or silica alumina, capable of causing dehydration and amination. In addition to dimethylamine (hereinafter referred to as "DMA"), monomethylamine (hereinafter referred to as "MMA") and trimethylamine (hereinafter referred to as "TMA") are produced as by-products by this reaction. The demand for these by-product methylamines is much smaller than that for DMA. For this reason, after being separated from the reaction product, these by-products are recirculated in the reaction system and reused.

Separation of dimethylamine from the methylamines is conducted by means of distillation. However, TMA forms a complicated azeotropic system together with ammonia, MMA and DMA, so that a very intricate large-scale distillation process is needed. As a result, the cost for energy consumed by the DMA-recovering process becomes extremely high. Examples of the recovery process are shown in detail, for instance, in "Manufacturing Process Charts, Revised Edition" (published by Kabushiki Kaisha Kagaku Kogyo-Sha on Apr. 25, 1978).

In order to reduce the production cost of DMA and to make the size of the equipment smaller, it is essential to suppress, as much as possible, the formation of by-product methylamines, especially the formation of TMA, and to promote the formation of DMA. However, the selectivities to the three methylamines are thermodynamically determined on the above-described conventional amorphous solid acid catalyst such as alumina or silica alumina. Under the typical reaction conditions, the ratio of TMA formation is considerably higher than that of DMA formation. For instance, in the case where the reaction temperature is 400° C. and the ratio of ammonia to methanol at the inlet of a reactor is 1:1 (weight ratio), the equilibrium weight ratio of the amines produced, calculated thermodynamically is MMA: DMA: TMA =0.284: 0.280: 0.436. In this case, the DMA selectivity defined by the following equation (1) is only 28.4%.

$$\text{DMA selectivity } (\%) = (2 \times W_D/D_{MW})/(W_M/M_{MW} + 2 \times W_D/D_{MW} + 3 \times W_T/T_{MW}) \times 100 \quad (1)$$

wherein $W_M$, $W_D$ and $W_T$ are the proportions by weight of MMA, DMA, and TMA produced, respectively, and $M_{MW}$, $D_{MW}$ and $T_{MW}$ represent the molecular weights of MMA, DMA and TMA, respectively.

For this reason, it is necessary to continually separate a large amount of MMA and TMA, and to recirculate, in the reaction system, these two methylamines along with a large amount of excess ammonia which is allowed to exist so that the reaction can proceed advantageously to DMA from the viewpoint of equilibrium.

In recent years, a variety of zeolite catalysts have been proposed aiming at solving the above problem. For example, there can be mentioned those catalysts which are described in the following patent publications: Japanese Laid-Open Patent Publication No. 69846/1981 which relates to zeolite A; Japanese Laid-Open Patent Publications Nos. 148708/1979 and 69846/1983 which relate to FU-1; U.S. Pat. No. 4,082,805 which relates to ZSM-5, ZSM-11 and ZSM-21; Japanese Laid-Open Patent Publication No. 113747/1981 which relates to ferrierite and erionite; Japanese Laid-Open Patent Publications Nos. 178951/1986 and 8358/1988 which relate to zeolite rho, ZK-5 and chabazite; Japanese Laid-Open Patent Publication No. 254256/1986 which relates to a catalyst having more improved DMA selectivity obtained by treating a specific zeolite with tetraethylorthosilicate or the like; Japanese Laid-Open Patent Publication No. 002740/1995 which relates to mordenite modified by a silylating agent; Japanese Laid-Open Patent Publications Nos. 46846/1981, 210050/1984, 049340/1983 and 9510/1994 which relate to mordenite whose DMA selectivity is improved by other various methods of modification; and U.S. Pat. No. 3,384,667 which relates to zeolite X, Y and L, levyhire, analcite, chabazite, gmelinite, erionite, ptilolite, ferrierite, clinoptilolite and the like.

Unlike the conventional amorphous catalysts such as silica alumina, all of the above zeolite catalysts give DMA selectivities higher than the thermodynamical equilibrium value. For instance, Japanese Laid-Open Patent Publication No. 210050/1984 discloses a process for selectively producing DMA, using mordenite. According to this process, when a 1:1 (weight ratio) mixture of ammonia and methanol is subjected to reaction which is carried out, for instance, by using mordenite catalysts having various cation compositions at a reaction temperature of 270° to 360° C., DMA selectivities of approximately 50% to approximately 60% are obtained. These selectivities correspond to values of approx. 2.0 to approx. 3.0 when converted to DMA equilibrium factors defined by the following equation (2):

$$\text{DMA equilibrium factor} = \quad (2)$$
$$(\text{DMA selectivity})/(\text{thermodynamical equilibrium DMA selectivity at the same reaction temperature})$$

Further, almost all of the above-described zeolite catalysts give DMA equilibrium factors of 1.2 to 4.0, and many of these factors are in the range of 1.5 to 3.5.

When such a zeolite catalyst is used for a continuous process for producing methylamines, the concentration of DMA in the outlet gas of a reactor becomes high because the DMA selectivity of the catalyst is high. As a result, the amount of a recycle material to be returned from the recovery process to the reactor is decreased. It becomes thus possible to decrease the total amount of materials which are fed from the reactor to the recovery process. This effect can be shown by comparing flow rates per unit process defined by the following equation (3):

flow rate per unit process = (3)
(total flow rate of materials to be fed from reactor to
recovery process (kgmol/hr))/(amount of DMA
manufactured (kgmol/hr))

The flow rate per unit process can be adjusted by controlling the amount of materials to be recycled from a recovery system to a reactor, in particular, the amount of ammonia. The degree of recycling of ammonia correlates with the atomic ratio N/C (the ratio of the number of nitrogen atoms to that of carbon atoms), that is, the atomic ratio between N and C contained in all those materials which are fed from the reactor to the recovery process. In order to reduce the load on the recovery process, it is necessary to decrease the flow rate per unit process as much as possible, that is, to lower the N/C ratio. However, it is unfavorable to drastically lower the N/C ratio from the view points of impurities produced as by-products, and the like.

The previously-mentioned zeolite catalysts are characterized in that they can decrease the flow rate per unit process without drastically lowering the N/C ratio as compared with the conventional catalysts of thermodynamical equilibrium controled type. From this point of view, it is necessary that the N/C ratio be generally 1.0 or more, preferably 1.3 or more. For instance, in the case where approx. 25 mol/hr, approx. 65 mol/hr and approx. 10 mol/hr of MMA, DMA and TMA are produced, respectively, at the N/C ratio of 2.0 by using zeolite catalysts having various DMA equilibrium factors, the flow rates per unit process are as follows:

| Catalyst | DMA Equilibrium Factor | Flow Rate per Unit Process |
| --- | --- | --- |
| Silica Alumina (Conventional) | 1.0 | 18 |
| Zeolite (1) | 1.5 | 13 |
| Zeolite (2) | 2.2 | 10 |

In this case, the essential purpose of the use of a zeolite catalyst is to make the flow rate per unit process lower, as much as possible, than at least the above-shown value of 18, which is the most typical flow rate per unit process when the conventional catalyst is used. However, it was found that when the zeolite catalyst is placed in an insulated reactor which has been used with the conventional catalyst, and a reaction is initiated at a temperature which is made low as much as possible (the inlet temperature of the catalyst bed: 250°–260° C.) so as to prevent the formation of coke materials, the catalyst is rapidly deactivated as will be shown later in Comparative Examples, giving rise to a very serious problem in practical use. The catalyst deactivation can be indicated by degeneration constant (ρ) according to the definitions represented by the following equations (4) and (5):

$$k_t = k_0 \exp(-\rho t) \quad (4)$$

wherein ρ: degeneration constant,
$k_t$: reaction rate constant when t days have passed,
$k_0$: reaction rate constant when the reaction is initiated; and $$\text{Reaction rate constant } k = FRT/P_0 V \cdot \ln(1/1-x) \quad (5)$$

wherein F: feed rate of methanol,
R: gas constant,
T: reaction temperature,
$P_0$: initial partial pressure of methanol,
V: volume of catalyst,
x: conversion rate of methanol.

When a fixed bed reactor is used as in the case of the above process, it is necessary, from the commercial point of view, that a catalyst can be continuously used at least for one year, desirably for two years or longer. If a catalyst has initial catalytic activity reasonably high enough for commercial use, it can be used until the catalytic activity is lowered to approximately half of the initial activity. In this case, the deterioration constant corresponding to a catalyst life of one year is approximately 0.0021. However, in the case where a zeolite catalyst is used with a reactor of conventional type, any zeolite catalyst shows a deterioration constant of 10 times or more the above-mentioned threshold value, as will be shown later in Comparative Examples. It is thus extremely difficult to continuously use a zeolitic catalyst for the commercial scale of production.

Thus, a principal object in this technical field is to develop a process for producing methylamines, in which a zeolite catalyst can be continuously used for a prolonged period of time.

SUMMARY OF THE INVENTION

An object of the present invention is to provide a process for producing methylamines using a zeolite catalyst, in which process the deactivation of the zeolite catalyst is suppressed so that the zeolite catalyst can be continuously used for a prolonged period of time.

We made earnest studies in order to develop the above-described process for producing methylamines, using a zeolitic catalyst. As a result, it was found that when a reaction is carried out in such a manner that a zeolite catalyst bed is divided into two or more sections either in series or in parallel and that the difference between the inlet and outlet temperatures of each catalyst bed is kept in a specific range while the reaction is carried out, the life of the catalyst can be drastically improved, and the above object can thus be attained. The present invention has been accomplished on the basis of this finding.

Thus, the present invention relates to a process for producing methylamines, comprising contacting methanol and ammonia, or methanol, a mixture of methylamines and ammonia, or a mixture of methylamines and ammonia, in a gaseous phase, with a bed of a zeolite catalyst, wherein, the catalyst bed is divided into two or more sub-beds connected in series and/or parallel and the difference between the inlet and outlet temperatures of each catalyst sub-bed is kept in the range of approximately 5° C. to approximately 70° C. while the reaction is carried out.

DETAILED DESCRIPTION OF THE PREFERRED EMBODIMENT OF THE INVENTION

Figure 1:
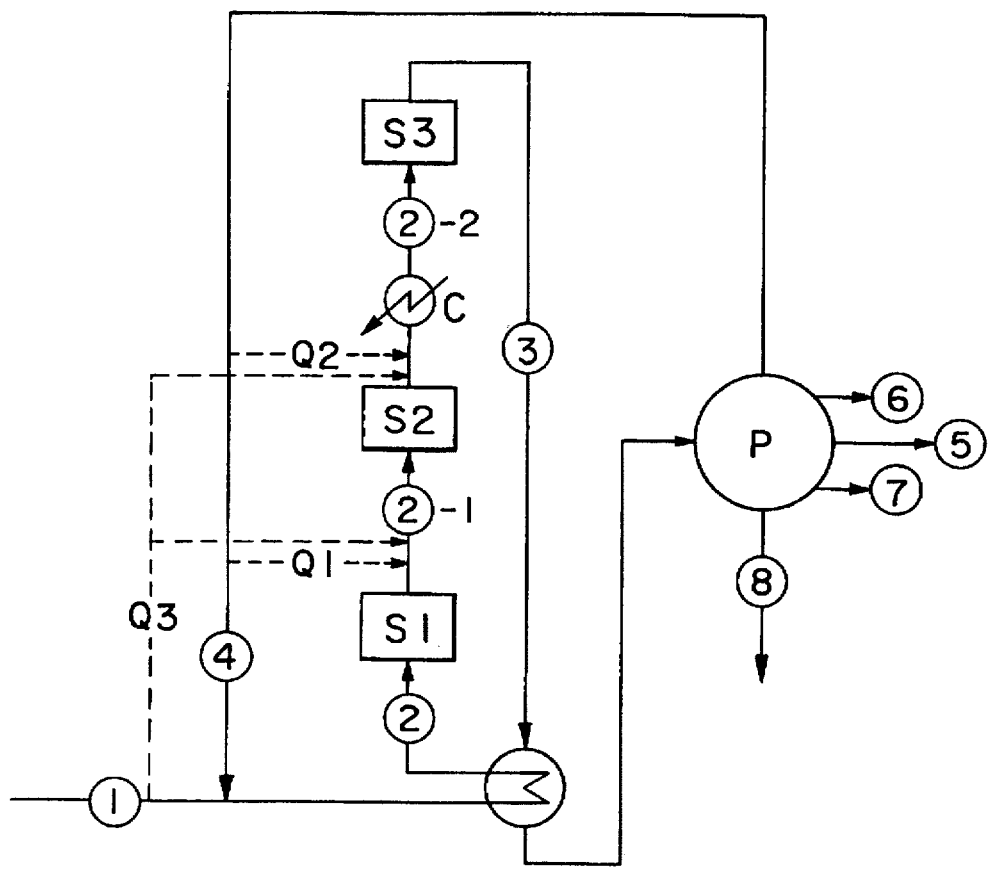
FIG. 1 is a diagrammatic flow sheet showing a process for producing methylamines according to the present invention.

The present invention will now be explained by referring to the accompanying drawings. A process in which a catalyst bed is divided into three sections or sub-beds connected in series as shown in FIG. 1 can be mentioned as one embodiment of the present invention.

Starting materials, methanol and ammonia (line ①), are joined with recycle material (line ④; gas and/or liquid) consisting essentially of unreacted ammonia, MMA and TMA, coming from recovery process (P). These materials, which are in the gaseous state, are fed (line ②) to the first section (S1) of the catalyst bed at a predetermined temperature via the steps of evaporation, heating, etc. A zeolite catalyst having a DMA equilibrium factor of 1.2 or more, preferably 1.5 or more is used as a catalyst. Specific examples of such a zeolite catalyst include mordenite, chabazite, levynite, zeolite rho, zeolite A, FU-1, erionite, ZSM-5, ZSM-11, ZSM-21, ZK-5 and montmorillonite, and zeolites obtained by modifying the mentioned ones. Among these, mordenite, chabazite and modified mordenite are most preferable. At the first section (S1), the starting materials and the recycle material react with each other. The outlet gas of the first section (line ②-1) is fed to the second section (S2) of the catalyst bed, and the outlet gas (line ②-2) of the second section is fed to the next section (S3). The unreacted starting materials and recycle material contained in the outlet gas react with each other at each section of the catalyst bed.

The reaction is carried out by controlling the inlet and outlet temperatures of each catalyst bed so that the difference between them will be kept in the range of approx. 5° C. to approx. 70° C., preferably approx. 10° C. to approx. 50° C., more preferably approx. 20° C. to approx. 40° C. Temperature differences larger than 70° C. would lead to shorter catalyst life, and temperature differences smaller than 5° C. would result in difficulty in obtaining desired methanol conversion.

In order to prevent the formation of impurities such as coke, it is desirable that the inlet temperature of the catalyst bed be approximated to the minimum temperature for initiating the reaction at a reasonable rate. It is desirable to control the inlet temperature to generally approx. 200° C. to approx. 350° C., preferably approx. 220° C. to approx. 330° C., more preferably approx. 230° C. to approx. 310° C.

It is preferable that the outlet gas of the catalyst bed be fed to the next catalyst bed after cooled. By this, the inlet temperature of the catalyst bed can be readily adjusted, and the operation for keeping the temperature of the catalyst bed can also be easily conducted.

The outlet gas can be cooled either by a condenser (C) using a refrigeration medium such as air, nitrogen gas or steam, or by a heat exchanger. Alternatively, the cooling of the outlet gas can be conducted by directly feeding the recycle material and/or a part of the starting materials (Q1, Q2 and/or Q3) to the outlet gas. The cooling of the outlet gas in the latter manner is particularly useful from the viewpoints of heat recovery and reduction in the cost of equipment.

The outlet gas (line ③) of the last section (S3) is heat-exchanged with the line for feeding the starting materials and the like, and then fed to the recovery process (P). At the recovery process, methylamines are respectively separated, by a plurality of distillation columns, from unreacted ammonia, water produced by the reaction, etc., and recovered. Unreacted ammonia, MMA and TMA are returned to the reactor as the recycle material (line ④).

It is preferable that the catalyst bed be divided into 2 to 10 sections, preferably 2 to 7 sections. When the effects of the present invention, the cost of equipment, and operating characteristics are taken into consideration, it is particularly preferable to divide the catalyst bed into 3 to 5 sections/sub-beds.

Further, with respect to the reaction at each catalyst sub-bed, it is preferable to control the reaction so that the difference between the conversion rates of methanol at the outlet and at the inlet of each sub-bed based on the conversion rate of methanol at the inlet of the first sub-bed will be in the range of 10% to 60%, preferably 15 to 50%. When the methanol conversion is lower than 10% the total number of catalyst sub-beds would be likely to be excessively higher, resulting in complexity in apparatuses, while, when the methanol conversion is higher than 60%, the catalyst life would be likely to be shorter.

The N/C ratio, viz. the ratio of the number of nitrogen atoms to that of carbon atoms, in the catalyst bed is from 0.8 to 3.0, preferably from 1.0 to 2.5, more preferably from 1.2 to 2.2. The N/C ratio lower than 0.8 would lead to production of by-products in higher amount, and the N/C ratio higher than 3.0 would result in increase in the amount of recycling and in the size of an apparatus used.

The reaction pressure is, in general, from normal pressure to 200 atom.

Figure 2:
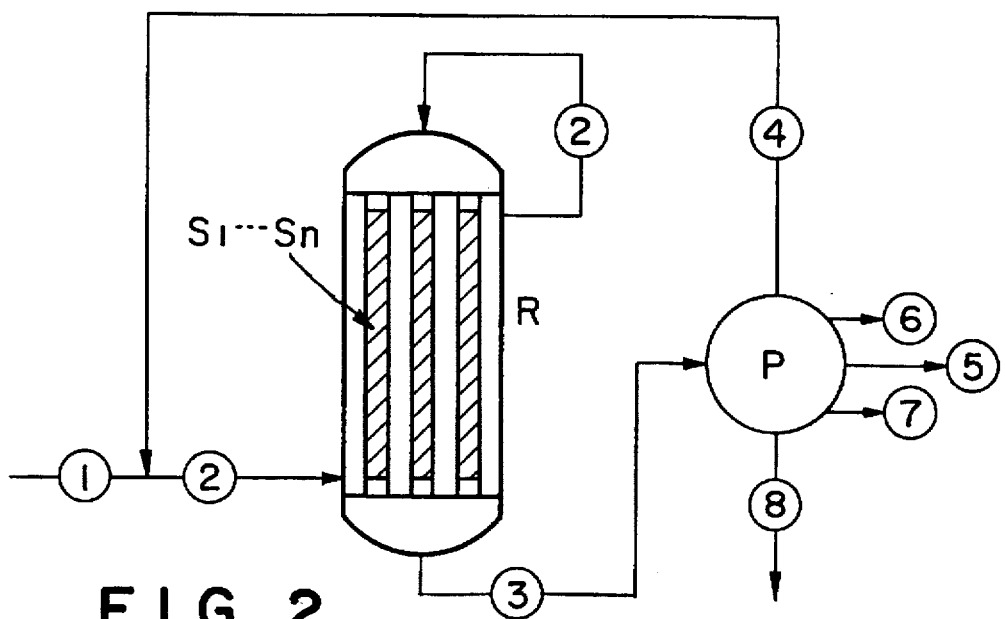
FIG. 2 is a diagrammatic flow sheet showing another process for producing methylamines according to the present invention.

Further, a process shown in FIG. 2 can be mentioned as another embodiment of the present invention. In this process is used a multiple-tube reactor (R), in which a plurality of reaction tubes are provided in parallel, and gas is made to flow outside the tubes. Starting materials, methanol and ammonia (line ①), are joined with recycle material consisting essentially of unreacted ammonia, MMA and TMA (line ④), coming from recovery process (P). These materials, which are in the gaseous state, are fed (line ②) at a predetermined temperature to the multiple-tube reactor from the lower part of the external shell thereof, via the steps of evaporation, heating, and the like. This gas is heat-exchanged, through the tube walls, with gas passing through the catalyst beds placed in the reaction tubes, flowing in the counter direction thereto. Thereafter, the gas is circulated in the upper part of the reactor, and introduced, from the top of the tubes, to the catalyst beds ($S_1 \ldots S_n$), thereby causing a reaction. After the gas thus fed is heat-exchanged with gas in the external shell of the reactor, it is fed as reaction product gas (line ③) to the next step, the recovery step (P), from the lower part of the reactor. At the recovery process, methylamines are respectively separated from unreacted ammonia, water produced by the reaction, etc. by a plurality of distillation columns, and recovered. Unreacted ammonia, MMA and TMA are returned as the recycle material (line ④) to the reactor.

Operational conditions for this embodiment with the catalyst sub-beds connected in parallel may be the same or similar to those for the previously mentioned embodiment with the catalyst sub-beds connected in series unless the former conditions interfere with the latter conditions.

One of the above-described zeolites can be used as the catalyst for the reaction. It is desirable that the difference between the inlet and outlet temperatures of the catalyst bed be small. It is therefore preferable to carry out the reaction by keeping the above difference in the range of approx. 5° C. to approx. 70° C., preferably approx. 5° C. to approx. 30° C., more preferably approx. 5° C. to approx. 20° C.

In order to prevent the formation of impurities such as coke, it is desirable that the inlet temperature of the catalyst bed be approximated to the minimum temperature for initiating the reaction at a reasonable rate. It is desirable to adjust the inlet temperature to generally from approx. 200° C. to approx. 350° C., preferably from approx. 220° C. to approx. 330° C., more preferably from approx. 230° C. to approx. 310° C.

The number of the reaction tubes is 2 or more, preferably 10 or more, more preferably 50 or more. In the case where this process is industrially employed, the number of the reaction tubes is from several hundreds to approximately 2,000, although it depends on the scale of production.

The total conversion rate of methanol at the catalyst layers is 80% or more, more preferably 85% or more.

The N/C ratio (the ratio of the number of nitrogen atoms to that of carbon atoms) in the catalyst bed is from 0.8 to 3.0, preferably from 1.0 to 2.5, more preferably from 1.2 to 2.2.

The reaction pressure is, in general, from normal pressure to 200 atom.

The present invention will now be specifically explained by referring to the following examples. However, the present invention is not limited by the following examples.

EXAMPLES

<Catalysts used>

Z1: H-form mordenite treated by steaming at 300° C. for 30 hours in granules of a diameter of approximately 5 mm.

Z2: Cation-form mordenite containing 0.7% by weight of K and 0.7% by weight of Ca in granules of a diameter of approximately 5 mm.

Z3: Mixture of Chabazite and erionite in granules of a diameter of approximately 5 mm.

A: Amorphous silica.alumina containing approximately 70% of silica in granules of a diameter of approximately 5 mm.

the tubes was made to be cooled, a continuous reaction experiment (for 2 weeks to one month) was carried out. Since this process has no recovery and recycling processes, the following composition was prepared and used as the starting material on the supposition that both recovery and recycling had been done in advance. Further, in order to make the heat dissipation per unit gas quantity in this process equal to that in the above examples, the surface of the reactor was kept heated. It was confirmed by Examples 3 and 6 that the processes in these examples were similar to each other.

|  | Composition of Starting Material (mol %) | | | |
| --- | --- | --- | --- | --- |
|  | Ammonia | Methanol | MMA | TMA |
| Examples 6 & 7 | 60 | 30 | 8 | 2 |
| Example 8 | 59 | 31 | 7 | 3 |

The results obtained in the above Examples 1 to 8 are shown in Table 1.

TABLE 1

| Example | Catalyst | No. of Cat. Sub-beds | Inlet Temp of *1 (°C.) | Temp Difference *2 (°C.) | N/C | Flow Rate *3 | Detriol. Const. ρ (×10⁻³) | DMA Eq. Factor |
| --- | --- | --- | --- | --- | --- | --- | --- | --- |
| 1 | Z1 | 2 | 250 | 40 | 2.0 | 11 | 1.4 | 2.2 |
| 2 | Z1 | 2 | 250 | 50 | 1.7 | 9 | 1.9 | 2.2 |
| 3 | Z1 | 3 | 250 | 35 | 1.7 | 9 | 1.0 | 2.2 |
| 4 | Z2 | 2 | 250 | 60 | 1.7 | 8 | 1.9 | 2.3 |
| 5 | Z2 | 3 | 250 | 40 | 1.7 | 8 | 0.9 | 2.3 |
| 6 | Z1 | 3 | 250 | 35 | 1.7 | 9 | 1.0 | 2.2 |
| 7 | Z3 | 3 | 260 | 30 | 1.7 | 11 | 1.2 | 2.0 |
| 8 | Z2 | 4 | 260 | 25 | 1.5 | 7 | 0.8 | 2.3 |

*1 Each Catalyst Sub-bed
*2 between Inlet and Outlet of Each Catalyst Sub-bed
*3 Per Unit Process Examples 1 to 5

Two or three reaction tubes provided in series as shown in FIG. 1 (an insulated reactor having a total capacity of approximately 20 m³) were filled with a zeolite catalyst. Gas between sections/sub-beds S1 and S2 was cooled by recycle material (liquid and gas) from recovery process (P), and gas between sections/sub-beds S2 and S3 was cooled by both the recycle material (liquid and gas) and air. Methanol and ammonia were fed at rates of 161 kgmol/hour and 87 kgmol/hour, respectively. Thus, a continuous reaction (for 2 weeks to one month) was carried out to obtain MMA, DMA and TMA at production rates of 20 kgmol/hour, 60 kgmol/hour and 7 kgmol/hour, respectively. The deterioration constant of the catalyst, shown in Table 1, was obtained from the change in the conversion rate of methanol, in accordance with the previously-mentioned equations (4) and (5).

Examples 6 to 8

By the use of a production process in which three or four reaction tubes, each having a diameter of approximately 1 inch, were connected in series, and gas in the space between Comparative Examples 1 and 2

An adiabatic reactor having a capacity of approximately 10 m³ was filled with the silica alumina catalyst (A). To this were fed methanol and ammonia at rates of 120 kgmol/hour and 65 kgmol/hour, respectively. Thus, a continuous reaction was carried out to produce MMA, DMA and TMA at production rates of 15 kgmol/hour, 45 kgmol/hour and 5 kgmol/hour, respectively. The deterioration constant of the catalyst in this case is shown in Table 2.

Comparative Examples 3 and 4

A continuous reaction was carried out in the same manner as in Example 1, except for the change that the gases between the catalyst sub-beds were not cooled. This run may thus correspond to one where an adiabatic reactor as in Comparative Example 1, the number of catalyst sub-beds being one, is used. The deterioration constant of the catalyst in this case is shown in Table 2.

Comparative Examples 5 to 7

A continuous reaction was carried out in the same manner as in Example 6, except for the change that the gases between the catalyst sub-beds were not cooled. Further, in order to make the heat dissipation per unit gas quantity in this process equal to that in the above Comparative Examples, the surface of the reactor was heated. It was confirmed by Comparative Examples 4 and 5 that the processes in these examples were similar to each other. These runs correspond to one where an adiabatic reactor as in Comparative Example 1, the number of catalyst sub-beds being one, is used. The deterioration constant of the catalyst in this case is shown in Table 2.

|  | Composition of Starting Material (mol %) | | | |
| --- | --- | --- | --- | --- |
|  | Ammonia | Methanol | MMA | TMA |
| Comparative Examples 5–7 | 60 | 30 | 8 | 2 |

The results obtained in the above Comparative Examples 1 to 7 are shown in Table 2.

This is a very unsatisfactory result from the practical point of view. In general, zeolite catalysts have extremely small pores as compared with amorphous catalysts, so that their catalytic activities are readily affected by coke materials deposited on the surface thereof. This is considered to be the reason why such an unsatisfactory result was obtained.

On the contrary, Examples 1 to 8 are the case where a reaction was carried out under the same conditions as in Comparative Examples except that the following were conducted in accordance with the process of the present invention: the zeolite catalyst bed was divided into 2 to 4 sections/sub-beds connected in series, and the difference between the inlet and outlet temperatures of each catalyst bed was kept in the range of 25° C. to 60° C. while the reaction was carried out. As a result, it was surprisingly found that the deterioration constant of the catalyst was lowered to 7 to 11. Such a value corresponds to a catalyst life of 1–2 years or longer. It can thus be confirmed that the life of the catalyst is dramatically improved to a period long enough to employ the present process for the industrial scale of production.

TABLE 2

| Comparative Example | Catalyst | No. of Cat. Sub-beds | Inlet Temp of *1 (°C.) | Temp Difference *2 (°C.) | N/C | Flow Rate *3 | Detriol. Const. $\rho$ $(\times 10^{-3})$ | DMA Eq. Factor |
| --- | --- | --- | --- | --- | --- | --- | --- | --- |
| 1 | A | 1 | 350 | 60 | 2.0 | 18 | 0.8 | 1.0 |
| 2 | A | 1 | 340 | 70 | 1.7 | 16 | 0.8 | 1.0 |
| 3 | Z1 | 1 | 250 | 100 | 2.0 | 11 | 17 | 2.2 |
| 4 | Z1 | 1 | 250 | 110 | 1.7 | 9 | 22 | 2.2 |
| 5 | Z1 | 1 | 250 | 110 | 1.7 | 9 | 22 | 2.2 |
| 6 | Z2 | 1 | 250 | 120 | 1.7 | 8 | 24 | 2.3 |
| 7 | Z3 | 1 | 260 | 105 | 1.7 | 11 | 23 | 2.0 |

*1 Each Catalyst Sub-bed
*2 between Inlet and Outlet of Each Catalyst Sub-bed
*3 Per Unit Process

[Consideration—the case where a catalyst bed is divided into sections/sub-beds connected in series]

Comparative Examples 1 and 2 are the case where a reaction was carried out by a conventional adiabatic reactor, using silica alumina, a conventional catalyst of thermodynamical equilibrium regulation type. The deterioration constant of the catalyst in this case was 0.8, which corresponds to a catalyst life of 2 years or longer. Comparative Examples 3 to 7 are the case where a reaction was carried out by the same equipment as in Comparative Examples 1 and 2, using various zeolitic catalysts. Although the inlet temperature of the catalyst layer was kept at as low as 250° C. to 260° C., which was approximately the minimum temperature for initiating the reaction at a reasonable rate, so as to prevent side reactions such as the formation of coke, the deterioration constant of the catalyst was surprisingly found to be at an extraordinarily high level of 17 to 24. Such a high value means that the life of the catalyst is only one or two months.

Examples 9 to 11

A multiple-tube reactor of heat-exchanger type (FIG. 2) in which 6 reaction tubes, each having a diameter of ½ inches, were provided in parallel was used. Each reaction tube in the reactor was filled with 25 ml of a zeolite catalyst to form catalyst sub-beds. To this was fed a starting material composition consisting of 61 mol % of ammonia, 29 mol % of methanol, 8 mol % of MMA and 2 mol % of TMA through the external shell of the reactor at a feed rate of 300 g/hour in the counterdirection to the flow of gas entering into the sub-beds through line ② and passing through the catalyst sub-beds ($S_1 \ldots S_6$), thereby carrying out a reaction for two weeks. The difference between the inlet and outlet temperatures of the catalyst sub-beds was 15° C. on the average. The results are shown in Table 3.

TABLE 3

| Example | Catalyst | No. of Cat. Sub-beds | Inlet Temp of *1 (°C.) | MeOH Conversion (%) | N/C | Flow Rate *2 | Detriol. Const. $\rho$ $(\times 10^{-3})$ | DMA Eq. Factor |
| --- | --- | --- | --- | --- | --- | --- | --- | --- |
| 9 | Z1 | 6 | 270 | 96 | 1.7 | 9 | 1.7 | 2.2 |
| 10 | 22 | 6 | 270 | 95 | 1.7 | 8 | 1.0 | 2.3 |
| 11 | 23 | 6 | 280 | 94 | 1.7 | 9 | 2.0 | 2.2 |

*1 Each Catalyst Sub-bed
*2 Per Unit Process

Comparative Examples 8 and 9

An adiabatic reactor having a diameter of one inch was filled with 100 ml of a zeolite catalyst. To this was fed a starting material composition consisting of 61 mol % of ammonia, 29 mol % of methanol, 8 mol % of MMA and 2 mol % of TMA from the lower part of the reactor at a rate of 200 g/hour, thereby carrying out a reaction for two weeks. The difference between the inlet and outlet temperatures of the catalyst bed was 90° C. on the average.

Comparative Examples 10 to 12

An adiabatic reactor of a diameter of one inch having an outer shell was used. The inner tube of the reactor was filled with 100 ml of a zeolite catalyst. To this was fed a starting material composition consisting of 61 mol % of ammonia, 29 mol % of methanol, 8 mol % of MMA and 2 mol % of TMA through the external shell of the reactor at a rate of 200 g/hour in the counterdirection to the flow of gas passing through the catalyst bed, thereby carrying out a reaction for two weeks. The difference between the inlet and outlet temperatures of the catalyst bed was 70° C. on the average.

The results obtained in the Comparative Examples 8 to 12 are shown in Table 4.

bed, flowing in the counterdirection to the feed gas. As a result, it was surprisingly found that the deterioration constant of the catalyst was improved to 1 to 2, which was almost 1/10 of that in Comparative Examples, although the inlet temperature of the catalyst bed was higher than that in Comparative Examples. Such a value corresponds to a catalyst life of 1 to 2 years. The present process can thus be adequately employed for the industrial scale of production.

According to the process of the present invention, the life of a zeolite catalyst for use in the production of methylamines can be remarkably improved, and the catalyst can be continuously used in the production for a long period of time at a low reaction temperature of 300° C. or lower. The production of methylamines can thus be advantageously conducted in the industrial scale.

What is claimed is:

1. In a process for producing methylamines, comprising contacting methanol and ammonia or methanol a mixture of methylamines and ammonia, or a mixture of methylamines and ammonia, in a gaseous phase, with a bed of a zeolite catalyst, the improvement which comprises the use of the zeolite catalyst such that the catalyst bed is divided into two or more sub-beds connected in series and/or parallel, and the

TABLE 4

| Comparative Example | Catalyst | No. of Cat. Sub-beds | Inlet Temp of *1 (°C.) | MeOH Conversion (%) | N/C | Flow Rate *2 | Detriol. Const. ρ (×10⁻³) | DMA Eq. Factor |
|---|---|---|---|---|---|---|---|---|
| 8  | Z1 | 1 | 240 | 97 | 1.7 | 11 | 22 | 2.0 |
| 9  | Z3 | 1 | 250 | 95 | 1.7 | 12 | 20 | 1.9 |
| 10 | Z1 | 1 | 250 | 96 | 1.7 | 10 | 12 | 2.1 |
| 11 | Z2 | 1 | 250 | 95 | 1.7 | 9  | 9  | 2.2 |
| 12 | Z3 | 1 | 260 | 94 | 1.7 | 11 | 10 | 2.0 |

*1 Each Catalyst Sub-bed
*2 Per Unit Process

[Consideration—the case where a catalyst bed is divided into sections/sub-beds connected in parallel]

Comparative Examples 8 and 9 are the case where methylamines were synthesized on a single bed of a zeolite catalyst by using a small-size equipment which was of the same type as a conventional adiabatic reactor used for the production of methylamines. Although the inlet temperature of the catalyst bed was kept at as low as 240° C. to 260° C., which was approximately the minimum temperature for initiating the reaction at a reasonable rate, so as to prevent side reactions such as the formation of coke, the deterioration constant of the catalyst was found to be at an extraordinarily high level of 20 or more. Such a level corresponds to a catalyst life of only about one month, and is far from the level suitable for practical use.

Comparative Examples 10 and 11 are the case where a single bed of a zeolite catalyst was provided in the inner tube of a double-tube reactor, and a reaction was allowed to proceed with heat-exchange of feed gas with gas passing through the catalyst bed, flowing in the counterdirection to the feed gas. In this case, the deterioration constant of the catalyst is approximately 10. Although this value is slightly improved as compared with Comparative Examples 8 and 9, it is still far from the level useful for practical use.

On the contrary, Examples 9 to 11 are the case where a reaction was carried out, in accordance with the process of the present invention, by a multiple-tube heat-exchanger-type reactor using a zeolite catalyst which had been divided into 6 sections/sub-beds connected in parallel, with feed gas being heat-exchanged with gas passing through the catalyst difference between the inlet and outlet temperatures of each catalyst sub-bed is kept in the range of approximately 5° C. to approximately 70° C. while the reaction is carried out.

2. The process according to claim 1, wherein the zeolite catalyst is one which can give a dimethylamine selectivity of 1.2 times or more the thermodynamical equilibrium value at a temperature at which the zeolite catalyst is used.

3. The process according to claim 1, wherein the zeolite catalyst is selected from the group consisting of mordenite, chabazite, levynite, zeolite rho, zeolite A, FU-1, erionite, ZSM-5, ZSM-11, ZSM-21, ZK-5 and montmorillonite, and zeolites obtained by modifying the mentioned ones.

4. The process according to claim 1, wherein the inlet temperature of the catalyst sub-bed is in the range of approximately 200° C. to approximately 350° C.

5. The process according to claim 1, wherein the N/C ratio which is a ratio of the number of nitrogen atoms to that of carbon atoms in the catalyst sub-bed is in the range of 0.8 to 3.0.

6. The process according to claim 1, wherein the catalyst sub-bed is connected in series.

7. The process according to claim 6, wherein the total number of the sub-beds of the catalyst bed divided is from 2 to 10.

8. The process according to claim 6, wherein a gas which is fed from a given catalyst sub-bed to the subsequent catalyst sub-bed connected in series is cooled.

9. The process according to claim 6, wherein a gas having undergone the reaction is treated so that the desired methylamine formed is recovered from the gas and at least a part of the remaining gas is recycled to the process and wherein a gas which is fed from a given catalyst sub-bed to the subsequent catalyst sub-bed connected in series is cooled by using recycle gas or liquid from purification process, or a part of starting material, ammonia or methanol.

10. The process according to claim 6, wherein the reaction at each catalyst sub-bed is so controlled that the difference between the conversion rate of methanol at the outlet and the inlet of each catalyst sub-bed based on the conversion rate of methanol at the inlet of the first catalyst sub-bed will be in the range of 10% to 60%.

11. The process according to claim 1, wherein the catalyst bed is divided into sub-beds in parallel inside a reactor.

12. The process according to claim 11, wherein the conversion rate of methanol is approximately 80% or more.

13. The process according to claim 11, wherein the total number of the sub-beds is 2 to 2,000.

* * * * *